United States Patent [19]

Leonard

[11] Patent Number: 4,741,832

[45] Date of Patent: May 3, 1988

[54] PURIFICATION APPARATUS AND METHOD EMPLOYING A REGENERABLE LIGAND

[75] Inventor: Edward F. Leonard, Bronxville, N.Y.

[73] Assignee: The Trustees of Columbia, University in the City of New York, New York, N.Y.

[21] Appl. No.: 610,368

[22] Filed: May 15, 1984

[51] Int. Cl.[4] .............................................. B01D 13/00
[52] U.S. Cl. .................. 210/638; 210/321.75; 210/321.8
[58] Field of Search ............... 210/632, 638, 433.2, 210/341.3, 643, 648, 321.75, 321.8

[56] References Cited

U.S. PATENT DOCUMENTS

| | | | |
|---|---|---|---|
| 3,842,000 | 10/1974 | Dawson | 210/23 |
| 3,993,558 | 11/1976 | Prochazka et al. | 210/28 |
| 4,056,467 | 11/1977 | Christen et al. | 210/632 X |
| 4,131,544 | 12/1978 | Elahi | 210/40 |
| 4,266,026 | 5/1981 | Breslau | 210/632 X |
| 4,303,531 | 12/1981 | Kawabata et al. | 210/663 |
| 4,353,992 | 10/1982 | Pannekeet | 210/674 X |
| 4,361,484 | 11/1982 | Larsson et al. | 210/632 |
| 4,375,414 | 3/1983 | Strahilevitz | 210/638 |
| 4,441,794 | 10/1983 | Schwinn et al. | 210/670 |
| 4,612,122 | 9/1986 | Ambrus et al. | 40/927 X |
| 4,637,880 | 1/1987 | Halbert | 210/638 |

*Primary Examiner*—Frank Spear
*Attorney, Agent, or Firm*—Brumbaugh, Graves, Donohue & Raymond

[57] ABSTRACT

An apparatus and method for purifying a fluid stream employ a bed of regenerable ligands affixed to one side of a semipermeable membrane. A ligate-laden fluid stream is conducted along the one membrane side, and the ligands selectively remove the ligates from the fluid stream by adsorption. A regeneration agent is conveyed to the ligand bed by diffusion across the membrane to break the ligand-ligate bonds and free the ligates. The freed ligates are rinsed from the vicinity of the regenerated ligand bed, which is now capable of adsorbing additional ligates.

18 Claims, 6 Drawing Sheets

PURIFICATION APPARATUS AND METHOD EMPLOYING A REGENERABLE LIGAND

BACKGROUND OF THE INVENTION

The use of adsorption to purify fluid streams is known. During the process of adsorption, an immobolized molecule (known as a "ligand") forms a chemical bond with another molecule carried by a fluid stream (known as the "ligate"). The ligand thus removes the ligate from the fluid stream, thereby purifying the fluid stream.

It is desirable that the ligand which is used have a highly selective binding constant for the target ligate, so that other substances in the fluid stream whose removal is not desired are not bound by the ligand. Highly selective ligands, however, tend to be costly.

One way of reducing the overall cost of a specific adsorption system is to employ a ligand which is capable of regeneration. A regenerable ligand has a binding constant which, under one set of circumstances, is high and which, under another set of circumstances, is low. During the latter circumstances, the ligand will release any bound ligate and is thereby made available for subsequent use.

Short cycles of adsorption and regeneration tend to minimize the ligand required to achieve a given rate of ligate removal (e.g., in grams per minute), and thus further reduce the overall cost of the adsorption system. Conventionally, the regeneration agent is conveyed to the ligand along the same fluid path which the ligate follows. Therefore, the possibility of shortening the cycle length is ultimately limited by the time required to displace a ligate-bearing fluid stream from the fluid path, replace it with the regeneration agent, then displace the regeneration agent, and finally reintroduce the ligate-bearing fluid stream. Regeneration by conventional methods thus tends to be time consuming and inefficient.

One of the principal objects of this invention is to provide an apparatus and system which purify a fluid stream by adsorption using a ligand which is repeatedly regenerated in a fast and efficient manner.

SUMMARY OF THE INVENTION

To this end, the invention provides a system and apparatus for purifying a fluid stream which employ a fixed ligand to adsorb a ligate carried in the fluid stream. The system and apparatus each includes a bed of ligands affixed to a semipermeable membrane. The ligand has a binding constant which, in the environment normally present in the fluid stream, will predictably bind the ligate and thus remove it from the fluid stream.

In accordance with the invention, an agent which regenerates the ligand is conveyed to the ligand bed by diffusion across the semipermeable membrane. The diffused agent breaks the ligate-ligand bond. The ligand is regenerated for subsequent use, and the ligate is freed for disposal.

The system and apparatus which embody the features of the invention are cycled through three operative modes.

In the first mode, the ligate-carrying fluid stream is conducted along the membrane to which the ligands are affixed. The desired ligate-ligand bonds are thus formed.

In the second mode, the regeneration agent is conveyed to the side of the membrane opposite to the fluid stream. The agent is transported to the ligands by diffusion across the membrane. The ligate-ligand bonds are broken, freeing the ligate and the ligand.

In the third mode, the freed ligates are removed from the apparatus.

The system and apparatus can be repeatedly and quickly cycled through the three modes, until the desired volume of fluid has been purified.

Before explaining the embodiments of the invention in detail, it is to be understood that the invention is not limited in this application to the details of construction and the arrangement of components as set forth in the following description or as illustrated in the accompanied drawings. The invention is capable of other embodiments and of being practiced or carried out in various ways. Furthermore, it is to be understood that the phraseology and terminology employed is for the purpose of description and should not be regarded as limiting.

DESCRIPTION OF THE PREFERRED EMBODIMENTS

Figure 1:
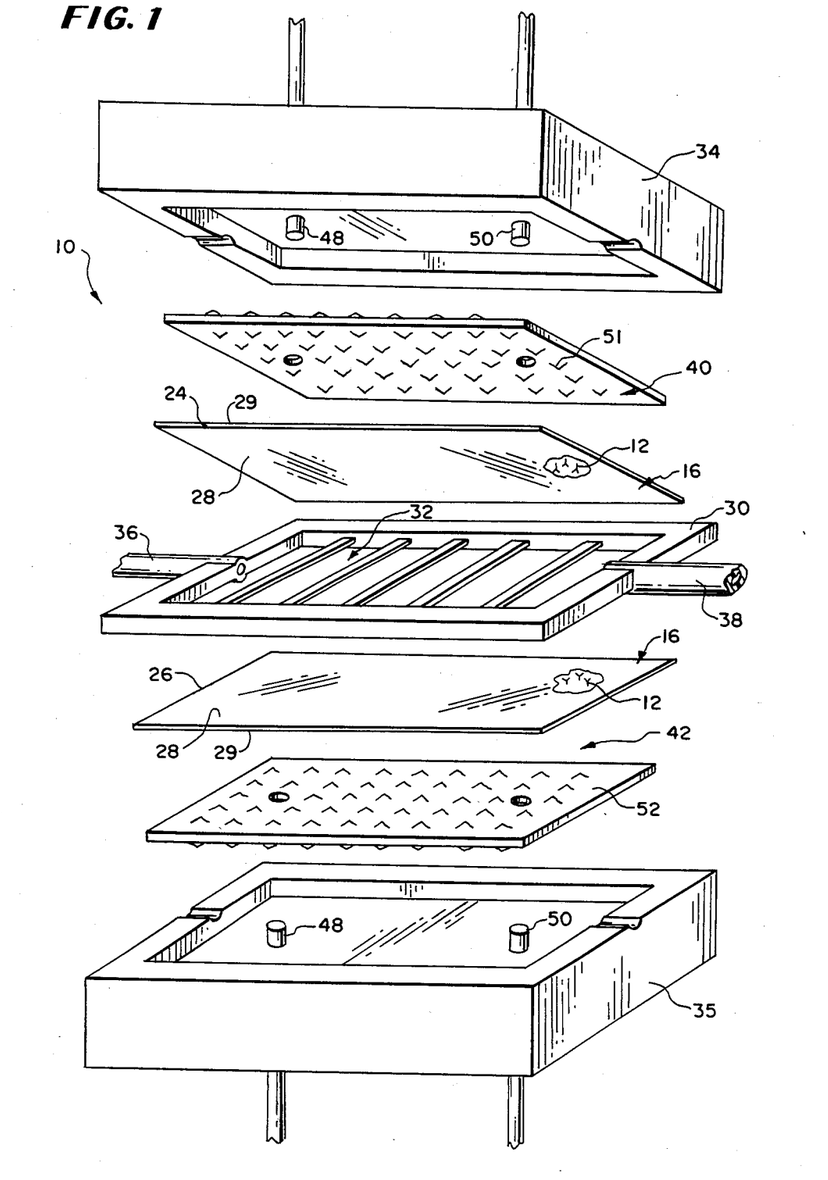
FIG. 1 is an exploded perspective view of the apparatus which embodies the feature of the invention.
Figure 2:
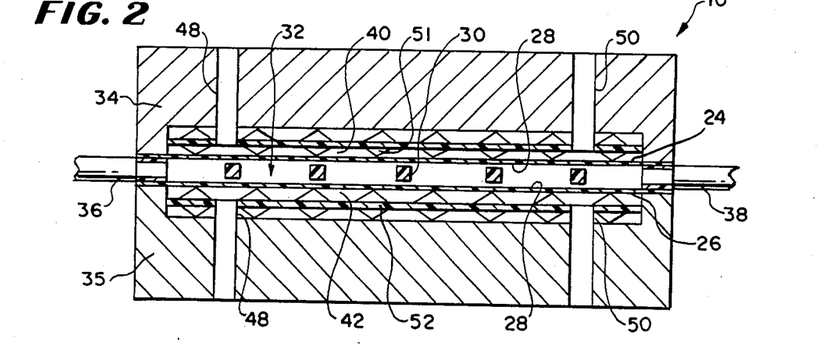
FIG. 2 is a side section view of the apparatus shown in FIG. 1 after assembly.

An apparatus 10 for purifying a fluid stream 11 by adsorption is shown in FIGS. 1 and 2.

Figure 3A:
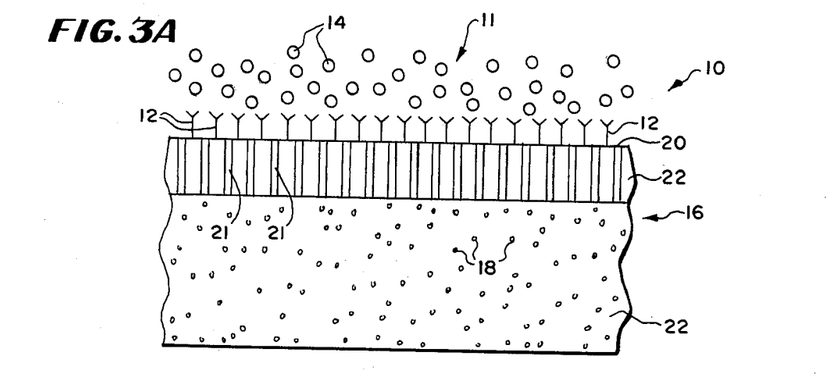
FIG. 3A is an enlarged diagrammatic section view of a portion of the membrane carried within the apparatus shown in FIGS. 1 and 2.
Figure 3B:
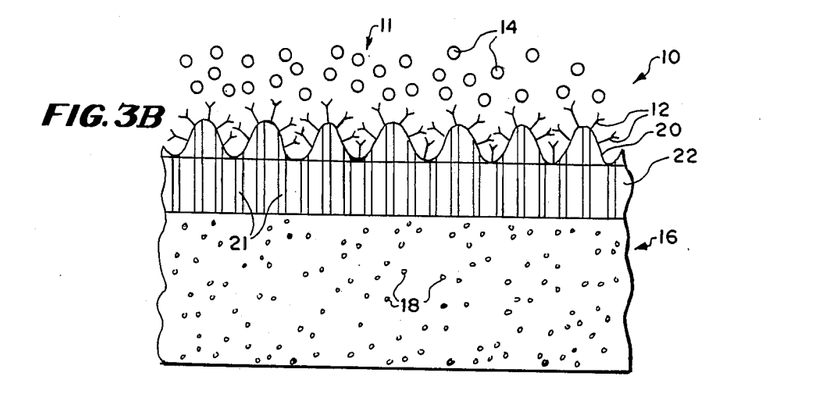
FIG. 3B is an alternate embodiment of the membrane portion of the apparatus shown in FIG. 3A.

In accordance with one aspect of the invention, the apparatus 10 includes one or more semipermeable membranes 16 on which immobilized molecules 12 (hereafter referred to as "ligands") are affixed in a predetermined pattern (see FIGS. 1 and 3A/3B).

In accordance with another aspect of the invention, the selected ligand 12 has a binding constant which, in the environment normally present in the fluid stream 11, will predictably form a chemical bond 13 with another molecule 14 carried in the fluid stream 11 (hereafter referred to as the "ligate"). Through this process (which is generally shown in FIG. 5B), the ligand 12 removes the ligate 14 from the fluid stream 11, thereby purifying it.

Figure 5A:
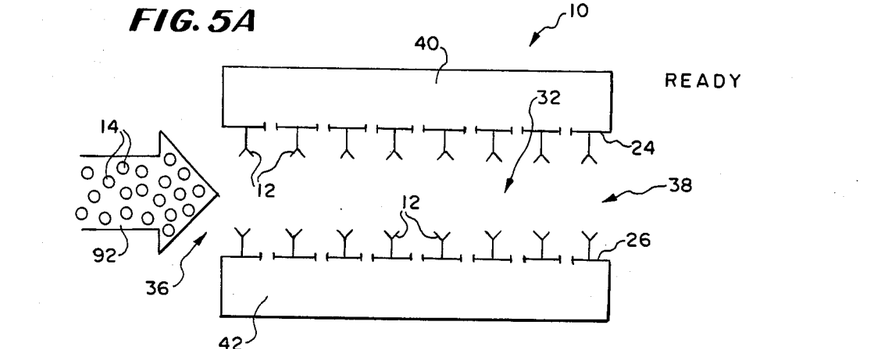
FIGS. 5A, 5B, 5C, 5D, and 5E are diagrammatic views of the operation of the apparatus as it is cycled through an Adsorption Mode, a Regeneration Mode, and a Rinse Mode in accordance with the features of the invention.
Figure 5B:
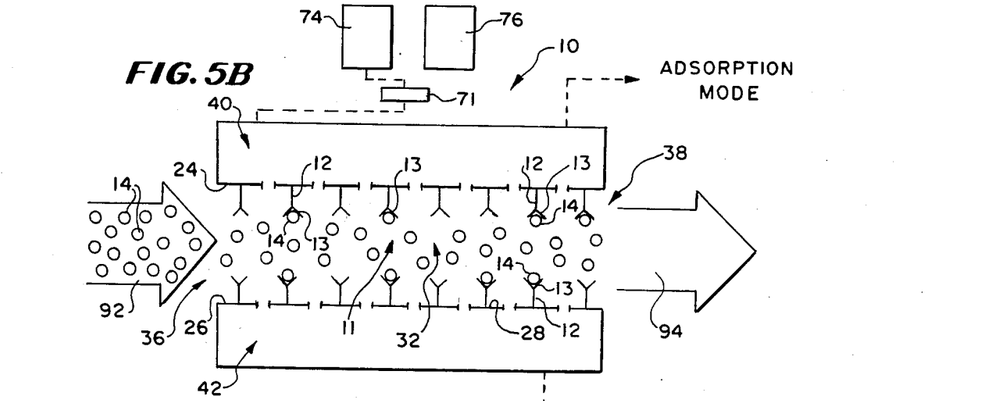

The binding constant of the selected ligand 12 will predictably decrease when the normal environment of the fluid stream 11 is purposely changed by exposure to a particular selected external agent 18. By lowering the binding constant, the agent 18 breaks the ligand-ligate bond 13 (a process which is generally shown in FIG. 5D), but not in a manner which destroys the ligand 12. The ligand 12 is regenerated for subsequent use, and the ligate 14 is freed for disposal (see FIG. 5E). The external agent 18 will hereafter be referred to as the "regeneration agent".

Figure 5C:
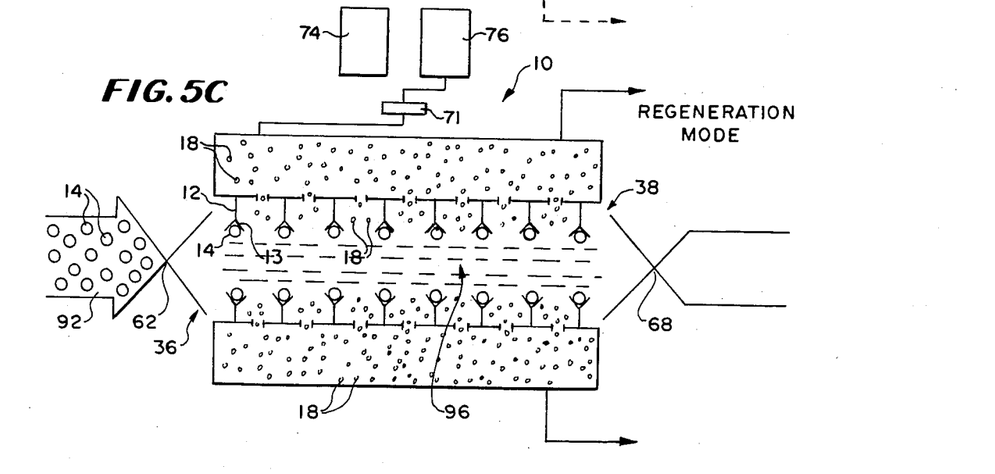
Figure 5D:
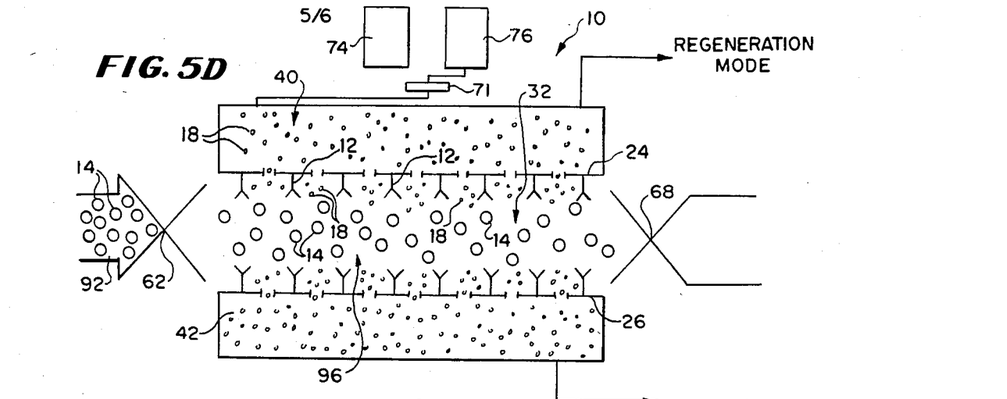

In accordance with yet another aspect of the invention, the regeneration agent 18 is conveyed into the apparatus 10 on the side of the membrane 16 opposite to where the ligand 12 is affixed (see FIGS. 5C and D). The agent 18 is transported to the ligands 12 by diffusion across the membrane 16.

The membrane 16 can be variously configured. For example, in one arrangement (not shown), it can be shaped as a hollow fiber. In this arrangement, the ligands 12 are affixed along the interior luminal surface of the bore.

Alternately, as shown in the illustrated embodiment, the membrane 16 is shaped as a flat sheet, and the ligands 12 are affixed to the surface which is exposed to the ligate-carrying fluid stream 11.

The ligands 12 can be affixed to the membrane 16 by various means. For example, a chemical coupling agent, such as 1,1'-carbonyl-diimidazole, can be used, as well as any other comparable method conventionally employed to bond a ligand to a fixed surface.

Regardless of the specific configuration of the membrane 16, the ligands 12 are preferably affixed along the surface of the membrane 14 which is exposed to the fluid stream 11. This assures that the ligands 12 are fully accessible to the ligates 14 carried in the fluid stream, as well as fully accessible to the regeneration agent 18 diffused across the membrane 16.

The permeability characteristics of the membrane 16 can vary. However, as shown in FIGS. 3A and 3B, in the surface region 20 of the membrane 16 where the ligand 12 is concentrated, the membrane 16 should be sufficiently porous to allow adequate contact between the ligate 12 and ligand 14. However, in the regions 22 of the membrane 16 spaced away from the ligands 12, the membrane 16 should be sufficiently impermeable to prevent convective transport of the fluid stream 11 across the membrane 16 in response to pressure differentials. By the same token, however, the membrane 16 should be sufficiently permeable to the regeneration agent 18 to allow diffusional transport across the membrane 16 when concentration differences exist.

The membrane 16 can be constructed in various ways to achieve the above objectives. In the embodiment shown in FIG. 3A, the membrane 16 is of uniform porosity across its width. In the embodiment shown in FIG. 3B, a multiple layer membrane 16 is used. In this arrangement, the surface region 20 is more porous than the interior regions 22. The ligands 12 are affixed to the more porous region 20.

It should be appreciated that the pores 21 of the membrane 16 can constitute straight, uniform paths as shown in FIGS. 3A and 3B, or they can constitute a series of nonuniform, tortuous paths.

The apparatus 10 may be variously constructed to support the membrane 16. In the illustrated embodiment, as best shown in FIGS. 1 and 2, the apparatus 10 includes a pair of semipermeable membranes 24 and 26, which are each configured as a flat sheet.

The facing surfaces 28 of the membranes 24 and 26 are kept a fixed distance apart by a spacer element 30 (see FIG. 2), thereby forming a fluid path 32 of predetermined thickness and volume between the membranes 24 and 26. The regenerable ligands 12 are affixed to the facing membrane surfaces 28 (see FIG. 1) in a predetermined pattern, as will be described in greater detail later.

It is desirable to minimize the spacing between the membrane surfaces 28 as much as possible, consistent with the desired fluid through-put of the apparatus 10. Preferably, the fluid path 32 should be no more than 200 microns across. This minimizes the volume of the fluid path 32. This also assures that the distance a given ligate 14 must travel across the width of the fluid path 32 to contact a ligand 12 can be traveled in the time it takes the ligate 14 to traverse the overall length of the fluid path 32.

In the illustrated embodiment, the apparatus 10 includes mating housing portions 34 and 35 which together enclose the membranes 24 and 26. The apparatus 10 also includes an inlet 36 for conducting the ligate-carrying fluid stream into the fluid path 32 and an outlet 38 for conducting the purified (i.e., ligate-free) fluid stream out of the fluid path 32.

The apparatus 10 further includes fluid passages 40 and 42 formed along the opposite surface 29 of the membranes 24 and 26, which do not face the fluid path 32.

The fluid passages 40 and 42 can be variously formed, depending upon the specific configuration of the membranes used. In the illustrated embodiment, a membrane support element 51 and 52 maintains an open flow path through the associated passage 40 and 42, as well as assures a uniform distribution of fluid within the associated passage 40 and 42.

Each passage 40 and 42 includes an inlet 48 for conducting fluid into the associated passage and an outlet 50 for conducting fluid out of the associated passage.

The apparatus 10 as heretofore described can constitute a single fluid path 32 with an associated pair of fluid passages, as shown in FIG. 2. However, two or more of the apparatus 10 shown in FIG. 2 can be stacked one atop the other to form multiple fluid paths and associated fluid passages. It should be appreciated that the axis of the fluid path 32 can extend either horizontally or vertically.

Figure 4:
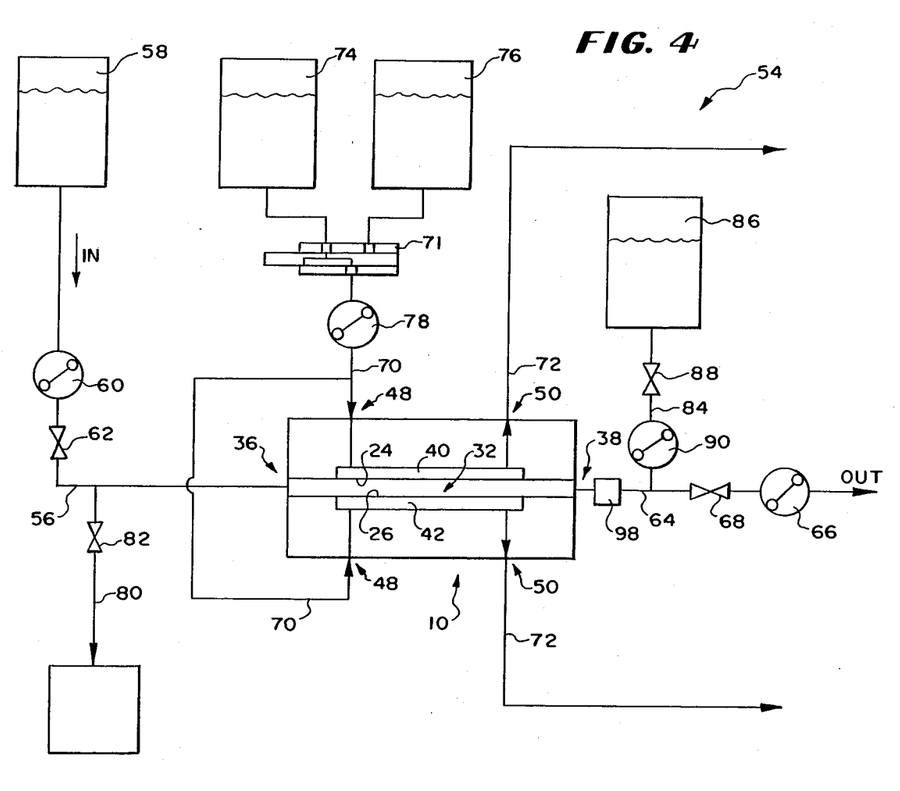
FIG. 4 is a system which embodies the features of the invention and which employs the apparatus shown in FIGS. 1 and 2.

The purification apparatus 10 as heretofore described can form a part of a purification system 54, which is shown in FIG. 4. The system 54 includes an inlet conduit 56 which connects the inlet 36 of the apparatus 10 with a source 58 of fluid which is to be purified. A pump 60 transports the fluid through the inlet conduit 56. An inline clamp 62 selectively opens and closes the inlet conduit 56 to fluid flow.

An outlet conduit 64 communicates with the outlet 38 of the apparatus 10 and conducts the purified fluid stream from the apparatus 10. A pump 66 can be employed to control the flow through the outlet conduit 64, if desired. An inline clamp 68 selectively opens and closes the outlet conduit 64 to fluid flow.

Inlet and outlet conduits 70 and 72 communicate, respectively, with the inlet and outlet 48 and 50 of each passage 40 and 42. The inlet conduit 70 selectively communicates through a suitable valve 71 with either the source 74 of a first solution or the source 76 of a second solution. A pump 78 serves to transport the selected solution through the inlet conduit 70 into the passages 40 and 42. The outlet conduit 72 transports the selected solution out of the passages 40 and 42 for discharge or recirculation.

The first solution in the source 74 has a chemical composition which mimicks the chemical composition of the fluid in the source 58, which is to be purified. In other words, the chemical composition of the first solution constitutes an environment favorable to the formation of the desired ligate-ligand bond 13.

The second solution in the source 76 constitutes the selected regeneration agent 18. As such, it has a chemical composition which differs from that of the fluid to be purified and, when in contact with the ligands 12, changes the environment to one which is unfavorable to the formation of the ligate-ligand bonds 13.

In accordance with the invention, a concentration difference exists between the second solution (being of a higher concentration) and the fluid in the fluid path 32 (being of a lower concentration). Because of this concentration difference, the second solution is diffused from the passages 40 and 42 across the membrane toward the fluid path 32.

The concentration difference may be achieved in various ways. The concentration difference can arise due to differences in ionic strengths, with the second solution having a higher concentration of ions than that of the fluid path 32. The concentration difference can also arise due to a difference in pH, with the second solution being more acidic or more alkaline than that of the fluid path 32. The concentration difference can also arise due to a difference in the concentration of molecules smaller than the ligate 14, with the second solution having the higher concentration of these molecules.

In the illustrated embodiment, pH differentials are employed to cause diffusional transport. In this arrangement, the first solution has a pH which generally equals the pH of the fluid to be purified, which, for the sake of description, is assumed to be neutral. The second solution has a pH which is less than (i.e., more acidic), and preferably significantly less than, the pH of the neutral fluid.

The system 54 further includes a discharge conduit 80 which, in the illustrated embodiment, communicates with the inlet conduit 56 between the inlet clamp 62 and the apparatus inlet 36. The discharge conduit 80 transports ligates 14 freed by the regeneration agent 18 away from the fluid path 32 for disposal. An inline clamp 82 selectively opens and closes the discharge conduit 80 to fluid flow. The discharge conduit 80 can, in an alternate arrangement, be positioned in communication with the outlet conduit 64.

The system 54 may also further include a rinse conduit 84 positioned on the side of the apparatus 10 opposite to the discharge conduit 80. In the illustrated embodiment, the rinse conduit 84 communicates with the outlet conduit 64 between the outlet clamp 68 and the outlet 38 of the apparatus 10. The rinse conduit 84 also communicates with a source 86 of a rinse solution. The rinse solution may be used to speed the transport of ligates 14 away from the fluid path 32 after regeneration. An inline clamp 88 and pump 90 selectively control the flow of rinse solution through the rinse conduit 84.

OPERATION

The operation of the apparatus 10 within the system 54 is shown sequentially in FIGS. 5A through 5E. As shown, the apparatus 10 is cycled through three operative modes.

The first mode (shown in FIG. 5B) is the Adsorption Mode. During this Mode, the ligate-carrying fluid stream (identified by numeral 92) is conducted through the fluid path 32 for purification. As shown in FIG. 5B, it is during this Mode that the ligate-ligand bonds 13 are formed along the facing surfaces 28 of the membranes 24 and 26. The ligate-free (i.e., purified) fluid stream (identified by numeral 94) is conducted from the apparatus 10.

The next mode (shown in FIG. 5C and 5D) is the Regeneration Mode. During this Mode, the regeneration agent 18 (from the source 76) is caused to diffuse across the membranes 24 and 26. It is during this Mode that the ligate-ligand bonds 13 formed during the preceding Adsorption Mode are broken. The diffused regeneration agent 18 frees the ligate 14 from the ligand 12 for disposal. At the same time, the ligand 12 is freed for subsequent use.

The next mode (shown in FIG. 5E) is the Rinse Mode. During this Mode, the freed ligates 14 and any diffused regeneration agent 18 which has entered the fluid path 32 are conveyed by fluid stream 96 from the fluid path 32 for disposal.

As shown in FIG. 5A, following the Rinse Mode, the apparatus 10 is again ready to commence another Adsorption Mode, followed by subsequent Regeneration and Rinse Modes.

Each of the three Modes will now be described in greater detail.

THE ADSORPTION MODE

At the start of the procedure, all inline clamps 62, 68, 82, and 88 are closed. To begin the Adsorption Mode, the clamps 62 and 68, at the inlet and outlet 36 and 38 of the apparatus 10, are opened as shown diagrammatically in FIG. 5A). The ligate-carrying fluid stream 92 is conducted by the pump 60 through the fluid path 32.

As the ligates 14 are exposed to the ligands 12, the ligate-ligand bonds 13 successively form along the membrane surfaces 28 (as shown in FIG. 5B). The purified, ligate-free fluid stream 94 is conducted through the outlet 38 and into the outlet conduit 64.

As shown in phantom lines in FIG. 5B, if desired during the Adsorption Mode, the valve 71 can be positioned to convey the first solution from the source 74 into each of the fluid passages 40 and 42. This will assure that diffusional transport does not occur across the membranes during this Mode.

A fixed volume of the first solution may be conveyed into the fluid passages 40 and 42 during the Adsorption Mode, or the solution may be continuously circulated through the passages 40 and 42, as shown in phantom lines in FIG. 5B.

The presence of the first solution in the fluid passages 40 and 42 is not essential for adsorption to occur within the fluid path 32. However, if the purified fluid stream is intended to be introduced into the human body, or if it is otherwise intended for a purpose requiring relatively stringent quality control standards, the presence of the first solution in the fluid passages 40 and 42 during the Adsorption Mode is preferred.

At the outset of the Adsorption Mode (see FIG. 5A), each ligand 12 is available to bind a ligate 14. Ligate-ligand bonds 13 form readily, and the ligate concentration in the stream 94 at the outlet 38 will be essentially zero (as shown in FIG. 5B). However, after bonds 13 are formed at more and more ligand sites, the ligands 12 will become more and more saturated with ligates 14, and the ligate concentration in the outlet stream 94 will begin to rise. This will be referred to as the "break-through point" of the apparatus 10. Eventually, adsorption will cease, and the ligate concentration in the outlet stream 94 will equal the ligate concentration in the inlet stream 92. The amount and nature of the ligand 12; the velocity of the fluid stream 92; and the initial concentration of the ligate 14 in the inlet stream 92 all contribute to the specific break-through point of the apparatus 10.

It is desirable to use a suitable device 98 (see FIG. 4) to monitor the concentration of ligates 14 in the outlet fluid stream 94 to detect when the break-through point has occurred. The monitor device 98 can employ ultra-violet spectrophotometry or any comparable technique for this purpose.

When the break-through point is reached, it is necessary to regenerate the ligand 12 so that purification of the fluid stream 92 can resume.

REGENERATION MODE

In accordance with the invention, the Regeneration Mode is begun as soon as possible after the system's break-through point is detected. As shown diagrammatically in FIG. 5C, the inlet and outlet clamps 62 and 68 are closed, leaving a volume of fluid 96 occupying the fluid path 32.

At this time, the valve 71 is positioned to introduce the second solution (i.e., the regeneration agent 18) from the source 76 into the fluid passages 40 and 42. A concentration difference is created across the membranes 24 and 26. As shown in FIG. 5C, the regeneration agent 18 has a molecular size sufficiently small enough to diffuse through the membranes 24 and 26 in response to the concentration differential created.

As the regeneration agent 18 diffuses across the membranes 24 and 26, it changes the environment surrounding the ligands 12, lowering the binding constant of the ligand 12. As shown in FIG. 5D, the ligand 12 then releases the previously bound ligate 14 into the surrounding fluid volume 96. The ligand 12 is thereby also freed for subsequent use.

The length of the Regeneration Mode is dependent upon the concentration differential obtained on opposite sides of the membranes 24 and 26, which controls the rate of diffusion. The length of the Mode is also dependent upon the effective pore size, or "tightness", of the membranes 24 and 26 and its thickness in the regions spaced away from the ligand bed 12. Both of these membrane-related factors also control the rate of diffusion. In this respect, attention is directed to Stevenson et al, "An Unsteady State Method for Measuring the Permeability of Small Tubular Membranes", *AIChE Journal*, Vol. 21, No. 6, pp. 1192 to 1199, November 1975. The length of the Regeneration Mode is further dependent upon the amount of the regeneration agent 18 and its inherent effectiveness, which control the speed and efficiency at which the ligate-ligand bonds 13 are broken.

By controlling these parameters, the rate of diffusion and the overall time of regeneration can be closely controlled.

Diffusional transport across the membrane constitutes a significantly faster and more efficient method of delivering the regeneration agent 18 to the ligands 12 than conventional practices, which rely upon transporting the regeneration agent 18 within the fluid path 32 to contact the ligands 12.

THE RINSE MODE

The fluid volume 96 occupying the fluid path 32 now contains all of the ligates 14 which have been removed during the preceding Adsorption Mode, as well as any diffused regeneration agent 18 which may have entered the fluid path 32 during the Regeneration Mode. Preferably, the rate of diffusion is controlled closely enough so that only a small volume of the regeneration agent 18 is present in the fluid volume 96.

The Rinse Mode is begun to convey the ligate-laden fluid volume 96 out of the apparatus 10. The Rinse Mode can be variously conducted.

In the illustrated embodiment (see FIG. 4), the discharge clamp 82 and outlet clamp 68 can be opened simultaneously to displace the ligate-laden fluid volume 96 with an equal volume of the purified fluid stream 94, which, in this arrangement, is back-flushed through the apparatus 10.

Alternately, if the discharge conduit 80 is situated at the outlet 38 of the apparatus 10, the ligate-laden fluid volume 96 can be replaced with an equal volume of the unpurified fluid stream 92.

Still alternately, the rinse solution can be conveyed through the rinse conduit 84 to displace the ligate-laden fluid volume 96 from the apparatus 10.

As the ligate-laden fluid volume is being rinsed from the apparatus 10, the valve 71 is positioned to again convey the first solution into the fluid passages 40 and 42. Diffusion across the membrane reverses, and the regeneration agent 18 is removed from the vicinity of the ligands 12 to return to the opposite surfaces 29 of the membranes 24 and 26. The environment favorable to the formation of ligate-ligand bonds 13 returns to the facing surfaces 28 of the membranes 24 and 26.

At this time, the Adsorption Mode can begin again, followed by yet another Regeneration and Rinse Mode, over and over until the desired volume of fluid has been purified.

Because the invention employs diffusion as the method of regenerating of the ligand 12, the apparatus 10 can be quickly and repeatedly regenerated during a purification procedure. In accordance with the invention, then, the amount of ligand 12 required for a given rate of ligand removal can be minimized to the fullest extent possible. At the same time, the various operating parameters of the system can also be optimized to the fullest extent possible.

In this regard, reference is made to the following Examples.

EXAMPLE I

The purpose of this Example is to illustrate how the various operating parameters associated with a given purification procedure affect the design of the apparatus 10 which embodies the features of the invention. The Example also demonstrates how the invention can be used to optimize the performance objectives of the purification procedure.

In this Example, the system will be used for the treatment of Myasthenia Gravis. Myasthenia Gravis is a disease in which antibodies carried by the blood plasma of a patient block normal neuro-muscular junctions. It has been observed that the removal of these antibodies from the patient's plasma exerts a beneficial therapeutic effect.

These antibodies (or ligates) can be removed from the plasma by adsorption, using an antibody-specific antigen (or ligand) affixed to a semipermeable membrane and regenerated in accordance with the invention.

The various clinical operating parameters associated with the extracorporeal treatment of Myasthenia Gravis by adsorption include:

(a) A typical patient has about $100 \times 10^{-9}$ moles of undesired antibodies per liter of plasma;

(b) For the patient's comfort and well being, an extracorporeal treatment time should not exceed 240 minutes;

(c) For the comfort of the patient, the rate at which plasma is removed for treatment should not exceed 70 cc/min. Typically, during the treatment, the whole blood will be withdrawn from the patent and passed through a centrifuge or filter to first separate the cellular components of the blood (red blood cells platelets, and leukocytes) from the plasma. The cellular components will be returned to the patient, while the plasma is next conveyed through the apparatus 10 as heretofore described to remove the offending antibodies. The purified, antibody-free plasma is then returned to the patient.

(d) The antigen known to bind the antibody associated with Myasthenia Gravis is the acetylcholine receptor obtained from the muscle tissue of the electric fish *torpedo californicus*. This ligand 12 is not easily obtained and is therefore costly. A system which embodies the feature of the invention can significantly reduce the cost of treatment. By regenerating the antigen N-times, the amount of antigen used can be reduced by 1/N. In this Example, the antigen will be regenerated 100 times during the 240 minute procedure, thereby reducing the antigen-related cost of the system by 1/100. This effectively reduces the cost of the ligand 12 required for a single treatment from more than $1,000 to the range of $10.

(e) Given the objective of regenerating 100 times, the overall treatment period will be divided into treatment cycles of 2.4 minutes each (240 minutes/100 regenerations). Each treatment cycle will, in turn, be divided into modes embodying the features of the invention, as follows:

| (1) | Adsorption Mode | 2.0 minutes |
|---|---|---|
| (2) | Regeneration Mode | 18 seconds |
| (3) | Rinse Mode | 6 seconds |

Figure 6:
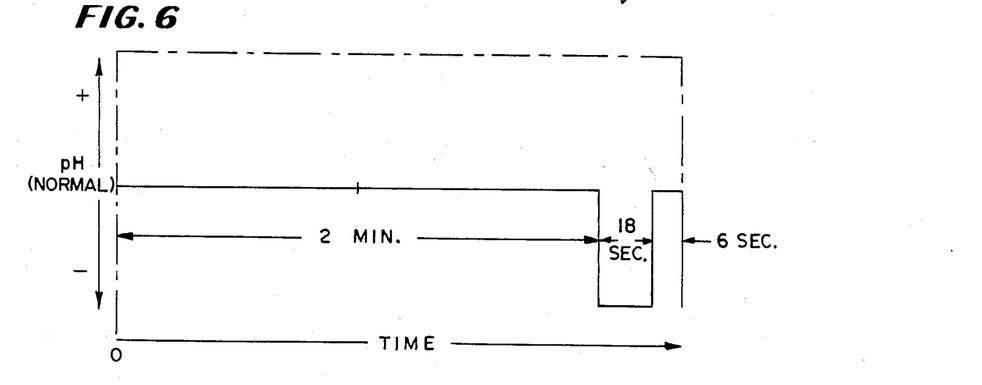
FIG. 6 is a graph showing the pH of the fluid conveyed through the apparatus as a function of time and illustrating the change effected in the pH to regenerate the apparatus in accordance with the features of the invention.

This treatment cycle is shown diagrammatically in FIG. 6.

From these operating goals and parameters, the size of the purification apparatus 10 can be calculated:

(f) The number of ligands (i.e., antigens) that are required to bond all of the the ligates (i.e., antibodies) traversing the apparatus 10 during each two minute Adsorption Mode ($N_L$) is:

$$N_L = \frac{2 \text{ Min} \times 70 \times 10^{-3} \text{ liters}}{\text{cycle min}} \times \frac{100 \times 10^{-9} \text{ nm}}{\text{liter}} \times$$

$$6 \times 10^{23} \text{ molecules (Avogadro's Number)}$$

$N_L = 8.4 \times 10^{15}$ ligands. This is the number of ligands which will be placed within the apparatus. In this Example, it is assumed that one ligand molecule will bind one ligate molecule.

(g) It is desirable to properly space the ligands upon the surface of the membrane to avoid overcrowding, which can, in turn, adversely effect the rate of adsorption. It is preferred that each ligand 12 occupy on the membrane an area of no less than 1600 $A^2$ ($1600 \times 10^{-16}$ cm$^2$). Therefore, the total membrane surface area ($M_A$) required is:

$$M_A = N_L \times 1600 \times 10^{-16} \text{ cm}^2$$

$$= 8.4 \times 10^{15} \text{ Ligands} \times 1600 \times 10^{-16} \text{ cm}^2$$

$$= 1344 \text{ cm}^2$$

(H) Since, in the illustrated embodiment, two flat sheets are used, $M_A$ can be divided in half, i.e., 672 cm$^2$.

(i) For a fluid path thickness of 0.01 cm, the volume of the fluid path ($V_P$) is:

$$V_P = 672 \text{ cm}^2 \times 0.01 \text{ cm}$$

$$V_P = 6.72 \text{ cc}$$

Figure 5E:
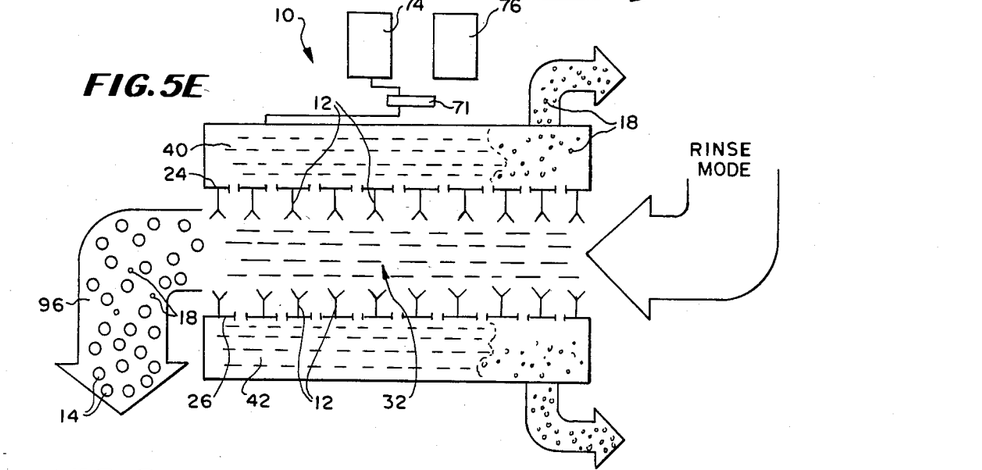

More particularly, at a plasma flow rate of 70 cc/minute through the above-described treatment apparatus 10, about 140 cc of plasma will be purified during each two minute Adsorption Mode. Of this volume, 6.72 cc of plasma will not be returned to the patient. Instead, this volume of plasma (constituting the fluid volume 96 shown in FIGS. 5C, D, and E) will be discharged during the Rinse Mode to convey all the ligates adsorbed during the preceding Adsorption Mode away from the apparatus 10. The overall plasma loss rate of the above-described apparatus 10 due to regeneration of the ligand is thus only 4.8%.

Furthermore, because the antigen is regenerated 100 times during the procedure, the cost of the antigen used for the treatment is reduced 100 times.

It should now be appreciated that the various operating parameters and purification objectives of the system and apparatus 10 made in accordance with the invention can be merged to obtain the desired performance results.

EXAMPLE II

The purpose of this Example is to illustrate that an apparatus 10 which embodies the features of the invention can be repeatedly cycled through successive Adsorption, Regeneration, and Rinse Modes.

The ligand 12 employed in the apparatus 10 was an acetylcholine analog. It was affixed to the facing surfaces of a pair of flat cellulose dialysis membranes 24 and 26. A fluid path 32 of 0.0126 mm separated the two membranes 24 and 26.

The ligate 14 was acetylcholine esterase present in a normal saline solution (pH 7.35) in a concentration of 8 mg/ml.

The apparatus 10 was used in association with a system 54 as shown in FIG. 4. The solution occupying the source 74 (i.e., the solution mimicking the stream to be purified) was normal saline. The solution occupying the source 76 (i.e., the regeneration agent 18) was a buffered citrate solution (pH 2.0). Normal saline solution was also employed as the rinse solution.

The apparatus 10 was operated through nine (9) successive cycles, each including an Adsorption Mode, a Regeneration Mode, and a Rinse Mode as heretofore described.

During each cycle, the following time periods were used:
- Adsorption Mode: 4.5 minutes
- Regeneration Mode: 1 minute
- Rinse Mode: 1 minute During each Adsorption Mode, the acetylcholine esterase solution was introduced into the apparatus at a flow rate of 3.6 ml/min. During each cycle, the concentration of the acetylcholine esterase in the fluid stream exiting the apparatus 10 was continuously monitored to detect the break-through point of the apparatus 10. The results are summarized in the Table.

During each Regeneration Mode, the citric acid buffer was introduced at a flow rate of 9.6 ml/min.

Figure 7:
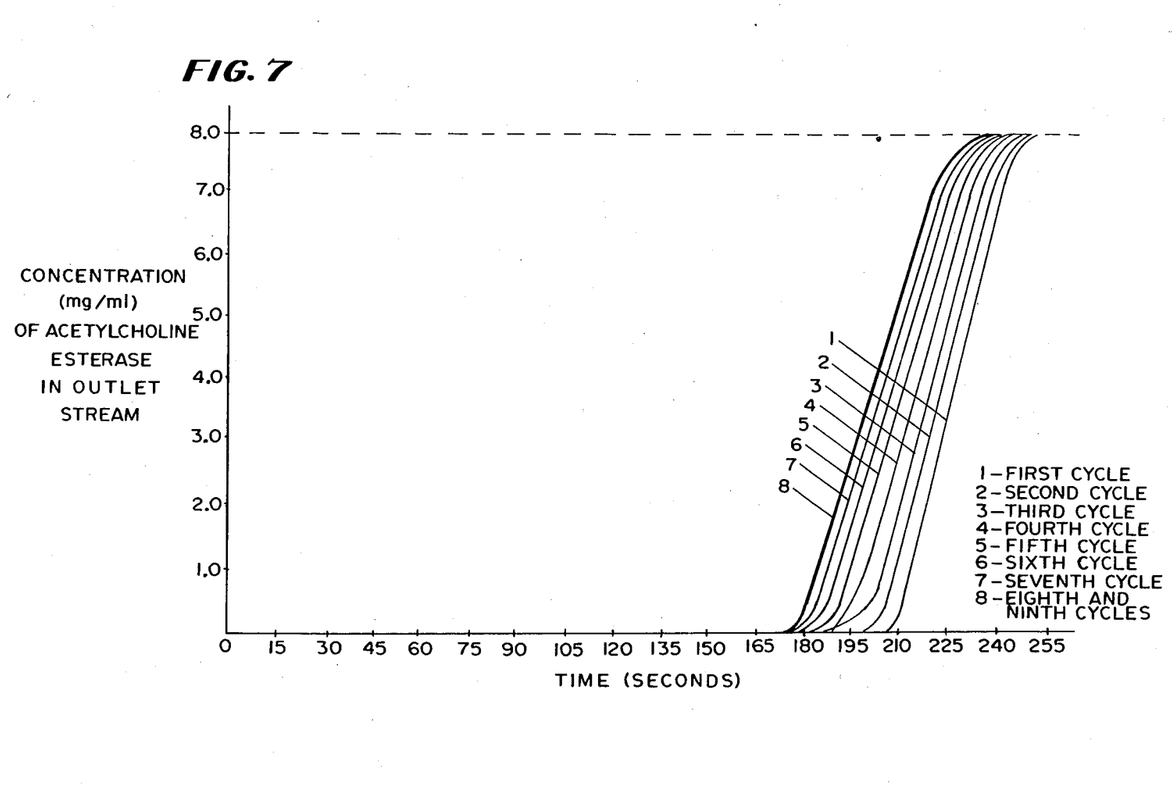
FIG. 7 is a graph showing the operation of a system and apparatus which embody the features of the invention.

The results are graphically shown in FIG. 7.

As shown in FIG. 7, during the Adsorption Mode of the first cycle, the concentration of acetylcholine esterase in the outlet stream was zero for a period of 210 seconds. After 210 seconds, however, the ligate concentration in the outlet stream began to increase, indicating that the break-through point had been reached. After 270 seconds, the ligate concentration in the outlet stream 94 equaled the ligate concentration in the inlet stream. A Regeneration Mode and a Rinse Mode followed to end the cycle.

In subsequent cycles, the break-through point was reached at a successively earlier time during the associated Adsorption Mode, until the eighth cycle. In the eighth and ninth cycles, the break-through point occurred after about 180 seconds of the associated Adsorption Mode, indicating that the apparatus had achieved a steady state operating condition.

It was observed that only about two percent (2%) of the regeneration agent 18 used during each Regeneration Mode "leaked" into the fluid stream and was discharged during the following Rinse Mode. The remainder of the regeneration agent diffused back through the membranes for subsequent use.

TABLE

THE BREAKTHROUGH POINT FOR THE ADSORPTION MODE OF NINE SUCCESSIVE CYCLES

| TIME (Seconds) | CYCLE NO. | | | | | | | | |
|---|---|---|---|---|---|---|---|---|---|
| | 1 C | 2 C | 3 C | 4 C | 5 C | 6 C | 7 C | 8 C | 9 C |
| 15 | 0 | 0 | | | | | | | |
| 30 | 0 | 0 | | | | | | | |
| 45 | 0 | 0 | | | | | | | |
| 60 | 0 | 0 | | | | | | | |
| 75 | 0 | 0 | | | | | | | |
| 90 | 0 | 0 | | | | | | | |
| 105 | 0 | 0 | | | | | | | |
| 120 | 0 | 0 | | | | | | | |
| 135 | 0 | 0 | | | | | | | |
| 150 | 0 | 0 | | | | | | | |
| 165 | 0 | 0 | | | | | | | |
| 180 | 0 | 0 | | | | | | | |
| 195 | 0 | 0 | 0.154 | 0.154 | 0.308 | 0.769 | 1.231 | 1.923 | 0.923 |
| 210 | 0 | 0.385 | 1.000 | 1.769 | 2.308 | 3.115 | 3.846 | 4.538 | 4.538 |
| 225 | 2.154 | 3.462 | 4.385 | 4.923 | 5.462 | 6.154 | 6.615 | 7.077 | 7.077 |
| 240 | 5.731 | 6.308 | 6.923 | 7.538 | 7.692 | 7.769 | 7.846 | 7.923 | 7.923 |
| 255 | 7.962 | 8.000 | 8.000 | 8.000 | 8.000 | 8.000 | 8.000 | 8.000 | 8.000 |
| 270 | 8.000 | 8.000 | 8.000 | 8.000 | 8.000 | 8.000 | 8.000 | 8.000 | 8.000 |

C = Concentration (in mg/ml) of acetycholine esterase in the outlet flow

I claim:

1. A method of purifying a fluid stream employing a regenerable ligand to adsorb a ligate carried in the fluid stream, said method comprising the steps of
   conducting the fluid stream along one surface of a membrane having affixed thereto the regenerable ligand, the membrane being sufficiently impermeable to the ligate-carrying fluid stream to prevent convective transport of the ligate-carrying fluid stream across the membrane in response to pressure differentials while being sufficiently permeable to a selected regeneration agent for the ligand to allow diffusional transport of the selected regeneration agent across the membrane when concentration differences exist, thereby forming a ligate-ligand bond on the one surface of the membrane,
   terminating the conduction of the fluid stream along the one surface of the membrane,
   diffusing the selected regeneration agent for the ligand across the membrane from the opposite surface of the membrane to the ligand to break the ligate-ligand bond, thereby freeing the ligate from the ligand, and
   rinsing the freed ligate away from the freed ligand.

2. A method according to claim 1 and further including a second diffusion step comprising
   after said rinsing step, diffusing the regeneration agent back across the membrane from the ligand to the opposite surface of the membrane.

3. A method according to claim 2
   wherein said second diffusion step includes exposing the opposite surface of the membrane to a solution having a concentration which differs from the concentration of the regeneration agent in an amount sufficient to cause the regeneration agent to diffuse back across the membrane away from the ligand.

4. A method according to claim 1 and further including the step of
   while said fluid stream conducting step is being carried out, maintaining an essentially zero concentration difference across the membrane to prevent diffusion while the ligate-ligand bond forms.

5. A method according to claim 1
   wherein said diffusion step includes exposing the opposite surface of the membrane to a regeneration agent having a concentration which differs from the concentration of the fluid stream in an amount sufficient to cause the regeneration agent to diffuse across the membrane toward the ligand.

6. A method of purifying a fluid stream employing a regenerable ligand to adsorb a ligate carried in the fluid stream, said method comprising the steps of
   conducting the fluid stream along one surface of a membrane having affixed thereto the regenerable ligand, the membrane being sufficiently impermeable to the ligate-carrying fluid stream to prevent convective transport of the ligate-carrying fluid stream across the membrane in response to pressure differentials while being sufficiently permeable to a selected regeneration agent for the ligand to allow diffusional transport of the selected regeneration agent across the membrane when concentration differences exist, thereby forming a ligate-ligand bond on the one surface of the membrane,
   terminating the conduction of the fluid stream along the one surface of the membrane, leaving a fixed volume of the fluid stream in contact with one membrane surface,
   exposing the opposite surface of the membrane to a solution containing the selected regeneration agent for the ligand and having a pH which differs from the pH of the fluid stream in an amount sufficient to cause the regeneration agent to diffuse across the membrane to break the ligate-ligand bond, thereby freeing the ligate into the fixed fluid stream volume, and rinsing the fluid stream volume containing the freed ligate and diffused regeneration agent away from the one surface of the membrane.

7. A method according to claim 6 and further including the step of while said fluid stream conduction step is being carried out, exposing the opposite surface side of the membrane to a solution having a pH generally equal to the pH of the fluid stream, thereby preventing diffusion across the membrane while the ligate-ligand bond forms.

8. A method according to claim 8 and further including the step of after said rinsing step, exposing the opposite surface of the membrane to a solution having a pH generally equal to the pH of the fluid stream to reverse the diffusion of the regeneration agent across the membrane.

9. An apparatus for purifying a fluid stream by the removal of ligates carried therein comprising a membrane having first and second surfaces, means defining a first fluid path along said first membrane surface for conveying the ligate-carrying fluid stream, a regenerable ligand affixed to said first membrane surface, said membrane being sufficiently impermeable to the ligate-carrying fluid stream to prevent convective transport of the ligate-carrying fluid stream across the membrane in response to pressure differentials while being sufficiently permeable to a selected regeneration agent for the ligand to allow diffusional transport of the regeneration agent across the membrane when concentration differences exist, and means defining a second fluid path along said second membrane surface for conveying the selected regeneration agent for said ligand in a concentration sufficiently different from the concentration of the fluid stream to diffuse across said membrane toward said ligand.

10. An apparatus according to claim 9 wherein said membrane is shaped as a hollow fiber, said first fluid path being the bore of said hollow fiber, said first membrane surface comprising the interior luminal surface of said hollow fiber, and said second membrane surface comprising the exterior surface of said hollow fiber.

11. An apparatus according to claim 9 wherein said membrane is shaped as a flat sheet having oppositely facing surfaces comprising said first and second membrane surfaces.

12. An apparatus according to claim 9 wherein said membrane is of uniform porosity between said first and second surfaces.

13. An apparatus according to claim 9 wherein said first surface of said membrane includes an exterior surface region and an interior region positioned between said exterior surface region and said second membrane surface, wherein said exterior surface region is more porous than said interior region, and wherein said ligand is affixed to said more porous, exterior surface region.

14. An apparatus according to claim 9 wherein a plurality of said ligands are affixed to said first membrane surface.

15. An apparatus according to claim 14 wherein each of said ligands occupies on said first membrane surface an area of no less than $1,600\text{A}^2$.

16. An apparatus according to claim 9 wherein said membrane includes a pair of membranes, each configured as a flat sheet and having first and second oppositely facing surfaces, wherein said first membrane surfaces of said pair of membranes are positioned in a facing, spaced apart configuration to form therebetween said first fluid path.

17. An apparatus according to claim 16 wherein said first fluid path between said pair of membranes is no more than 200 microns across.

18. A system for purifying a fluid stream employing a regenerable ligand to adsorb a ligate carried in the fluid stream, said system comprising an apparatus as defined in claim 9 inlet means for conducting the ligate-carrying fluid stream into said first fluid path of said apparatus to form a ligate-ligand bond on said first membrane surface, outlet means for conducting the ligate-free fluid stream from said first fluid path, means for conducting the selected regeneration agent for said ligand into said second fluid path for diffusion across said membrane to break the ligate-ligand bond, thereby freeing within said first fluid path the ligate from the ligand, and means communicating with one of said inlet means and said outlet means for transporting ligates freed by the regeneration agent away from said first fluid path.

* * * * *

UNITED STATES PATENT AND TRADEMARK OFFICE
CERTIFICATE OF CORRECTION

PATENT NO. : 4,741,832
DATED : May 3, 1988
INVENTOR(S) : Edward F. Leonard

It is certified that error appears in the above-identified patent and that said Letters Patent is hereby corrected as shown below: On The Title Page:

First page, Item 73, delete the comma after "Columbia"

Col. 3, line 33, "membrane 14 should be --membrane 16--

Col. 3, line 43, "ligate 12 and ligand 14" should be --ligate 14 and ligand 12--

Col. 6, line 37 "as" should read --(as--

Col. 8, line 47, "ligand" should be --ligate--

Col. 9, line 56 "the the" should be --the--

Col. 13, line 9, delete "side"; and

Col. 13, line 14, "claim 8" should read --claim 6--.

Signed and Sealed this

Twenty-fifth Day of October, 1988

Attest:

DONALD J. QUIGG

*Attesting Officer*  *Commissioner of Patents and Trademarks*